United States Patent
Svanberg et al.

(10) Patent No.: US 10,261,008 B2
(45) Date of Patent: Apr. 16, 2019

(54) DEVICE FOR HOLDING A LIGHT GUIDE, METHOD FOR MANUFACTURING SUCH A DEVICE AND AN OPTICAL FLOW CELL INCORPORATING SUCH A DEVICE

(71) Applicant: GE HEALTHCARE BIO-SCIENCES AB, Uppsala (SE)

(72) Inventors: Henrik Svanberg, Uppsala (SE); Bjorn A. Johansson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 15/564,612

(22) PCT Filed: Apr. 8, 2016

(86) PCT No.: PCT/EP2016/057858
§ 371 (c)(1),
(2) Date: Oct. 5, 2017

(87) PCT Pub. No.: WO2016/162544
PCT Pub. Date: Oct. 13, 2016

(65) Prior Publication Data
US 2018/0088026 A1    Mar. 29, 2018

(30) Foreign Application Priority Data

Apr. 10, 2015 (GB) .................................. 1506132.8

(51) Int. Cl.
*G01N 1/10* (2006.01)
*G01N 21/05* (2006.01)
(Continued)

(52) U.S. Cl.
CPC ............ *G01N 21/05* (2013.01); *G02B 6/0001* (2013.01); *G02B 6/36* (2013.01); *G02B 6/38* (2013.01); *G02B 6/381* (2013.01); *G02B 6/3833* (2013.01)

(58) Field of Classification Search
CPC ........... G01N 2021/0346; G01N 21/05; G01N 21/0303; G01N 21/53; G01N 2201/08;
(Continued)

(56) References Cited

U.S. PATENT DOCUMENTS

| 4,186,999 A | 2/1980 | Harwood et al. |
| 4,422,716 A | 12/1983 | Morimoto et al. |

(Continued)

FOREIGN PATENT DOCUMENTS

| EP | 0466077 A1 | 1/1992 |
| JP | S 63237005 A | 10/1988 |

(Continued)

OTHER PUBLICATIONS

PCT International Search Report and Written Opinion for PCT Application No. PCT/EP2016/057858 dated Jun. 10, 2016 (10 pages).
(Continued)

*Primary Examiner* — Hoa Q Pham
(74) *Attorney, Agent, or Firm* — Eversheds Sutherland (US) LLP

(57) ABSTRACT

The present invention relates to a method for manufacturing a device for holding a light guide, for use in a flow cell, with the steps of providing a light guide holder having a first end and a second end connected by a longitudinal through hole with a narrow portion at the first end having a first diameter and a wide portion at the second end having a second diameter, the first diameter being smaller than the second diameter, and the narrow portion and wide portion being connected by a tapering portion, inserting a light guide into the through hole so that a first end of the light guide extends from the first end to the second end of the light guide holder, inserting a substance into at least part of the wide portion of the through hole, Inserting a tube between the light guide and the light guide holder, and fix the light guide in relation to the holder by means of the substance. The invention also relates to a device for holding a light guide.

20 Claims, 7 Drawing Sheets

(51) Int. Cl.
*G02B 6/36* (2006.01)
*G02B 6/38* (2006.01)
*F21V 8/00* (2006.01)

(58) Field of Classification Search
CPC .... G01N 30/74; G02B 6/0001; G02B 6/3833; G02B 6/381
USPC .......... 356/244, 246, 335–343, 432–440, 73, 356/73.1; 385/31, 15, 84
See application file for complete search history.

(56) References Cited

U.S. PATENT DOCUMENTS

| | | | | |
|---|---|---|---|---|
| 4,726,681 | A | * | 2/1988 | Webb ................. G01N 15/0205 356/338 |
| 5,187,762 | A | | 2/1993 | Matsuura et al. |
| 8,649,005 | B2 | * | 2/2014 | Tormod ................. G01N 21/05 356/246 |
| 2002/0154309 | A1 | * | 10/2002 | Walker ............... G01N 21/0303 356/436 |
| 2007/0041009 | A1 | * | 2/2007 | Iwano .................... G01N 30/74 356/246 |
| 2010/0129647 | A1 | | 5/2010 | Bhagavatula et al. |
| 2018/0067040 | A1 | * | 3/2018 | Svanberg ............... G01N 21/05 |

FOREIGN PATENT DOCUMENTS

| | | |
|---|---|---|
| WO | 00/48023 A1 | 8/2000 |
| WO | 2004/017115 A1 | 2/2004 |
| WO | 2011/093775 A1 | 8/2011 |

OTHER PUBLICATIONS

GB Search Report for GB Application No. 1506132.8 dated Jun. 30, 2015 (5 pages).
Kyrocera, "Standard Ferrule Product List," 2009, http://global.kyocera.com/prdct/semicon/semi/std_pkg/pdf/kyocera-ferrule-e.pdf.

* cited by examiner

DEVICE FOR HOLDING A LIGHT GUIDE, METHOD FOR MANUFACTURING SUCH A DEVICE AND AN OPTICAL FLOW CELL INCORPORATING SUCH A DEVICE

CROSS REFERENCE TO RELATED APPLICATIONS

This application claims the priority benefit of PCT/EP2016/057858 filed on Apr. 8, 2016 which claims priority benefit of Great Britain Application No. 1506132.8 filed Apr. 10, 2015. The entire contents of which are hereby incorporated by reference herein.

TECHNICAL FIELD

The present invention relates to a device for holding a light guide and to a method for manufacturing such a device. The invention further relates to a flow cell incorporating such a device.

BACKGROUND

Optical flow cells are used within a plurality of technical fields where a solution is allowed to flow across a detector that serves to determine a concentration of a substance within the solution. Examples of such technical fields are fluid chromatography and filtering, among others.

The detectors used in the flow cells are generally optical detectors, having a first light guide with an exit surface where light is emitted and a second light guide with an entrance surface where the light is received. The distance between the exit surface and entrance surface can be relatively long for solutions of lower concentration, but in order to achieve reliable detection also for solutions of high concentration the distance should be smaller, typically in the range of 0.1-0.2 mm. To achieve satisfactory quality of measurements, the distance must be kept constant and is not allowed to deviate from a set value more than 5%.

To enable precision when manufacturing and mounting detectors, the light guides used should be held by light guide holders that can be fastened in a detector or a flow cell directly. However, to manufacture such a light guide holder with high precision is difficult, and care must be taken during insertion to prevent damages such as scratches or distortions to the shape of the light guide. This would otherwise result in a significantly lowered performance of the light guide and the measurements performed in the flow cell. Thus, it is a common problem to ascertain that no damage has been done to a light guide during mounting and that the light exit surface or light entrance surface that is to be used for measurements has not been scratched or otherwise damaged. There is a constant need for improvements within this area and for light guide holders that can overcome these drawbacks.

SUMMARY OF THE INVENTION

The object of the present invention is to eliminate or at least to minimize the disadvantages described above. This is achieved through a method and device as defined in the independent claims. Thereby, the light guide can be mounted in the light guide holder in a reliable way without risking damage to the light guide itself, thanks to the protection of the guiding member. The light guide holder can also be made without requiring the drilling of a long, narrow hole but rather using a smaller portion of a narrow width and a larger portion of a larger width, in which the light guide is fixed by the substance. Thus, manufacture of the light guide holder itself can also be facilitated. According to an aspect of the invention, the first diameter is less than 10% larger than a light guide diameter. Thereby, the light guide can be held securely in the narrow portion without requiring additional fixing.

According to another aspect of the invention, the light guide is fixed along a center of the through hole before the substance is inserted. Thereby, the light guide is held straight and distortion of the light transmitted through the light guide can be avoided.

According to yet another aspect of the invention, the substance is an inert adhesive with a viscosity of 400 cPs or less. Thereby, the insertion of the tube is facilitated and an undesired reaction of the adhesive with other substances during measurements performed when the device is inserted in a measuring device can be prevented.

According to yet another aspect of the invention, the step of inserting the guiding member into the through hole is performed by inserting the guiding member at the second end and using the tapering portion to guide the guiding member towards the narrow portion at the first end. Thereby, the insertion of the light guide into the narrow portion is facilitated and the flow of substance during mounting is improved.

More advantages and benefits of the present invention will become readily apparent to the person skilled in the art in view of the detailed description below.

DRAWINGS

The invention will now be described in more detail with reference to the appended drawings, wherein:

FIG. 3a shows a cross-sectional view of the device for holding a light guide according to the invention of;

FIG. 3b shows a planar view of the light guide holder of FIG. 3a;

FIG. 4b shows a cross-sectional perspective view of the measuring device of FIG. 4a;

FIG. 6 shows a planar view from above of the measuring device of FIG. 4a; and

DETAILED DESCRIPTION

Figure 3A:
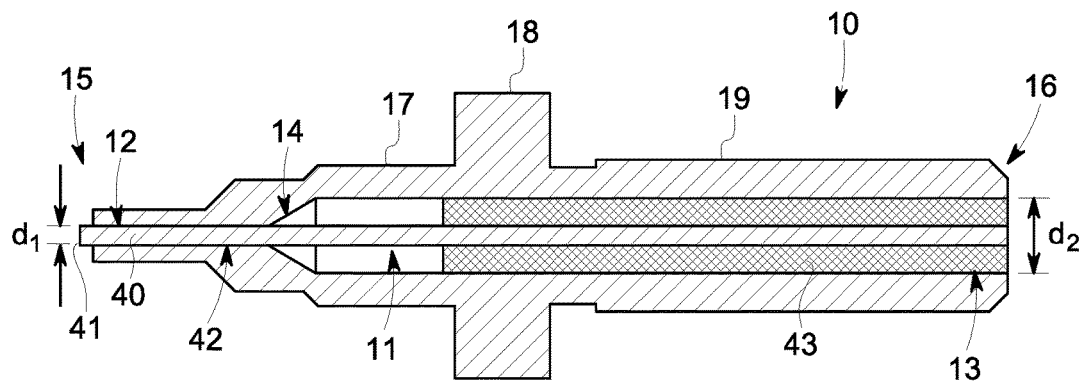
Figure 3B:
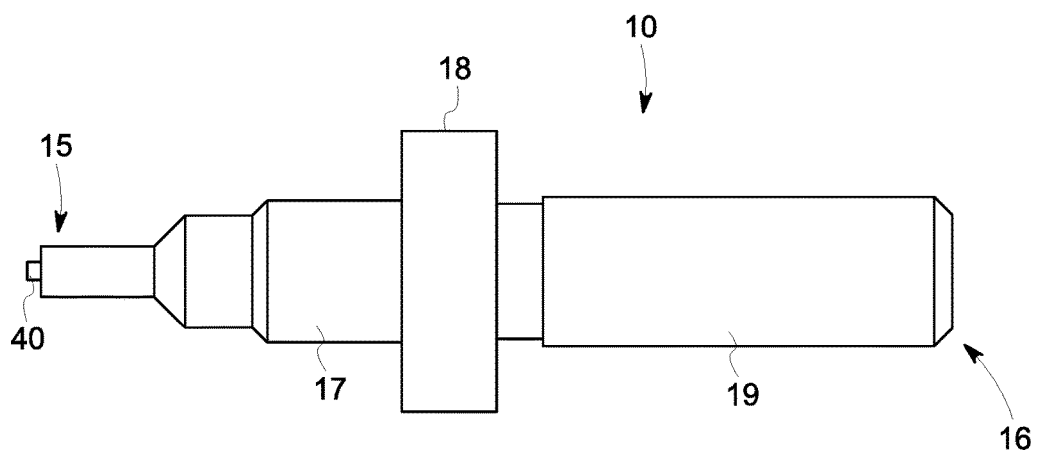

The device for holding a light guide is disclosed in FIG. 3a-3b, and the other figures show examples of how the device can be used in an optical flow cell and a measuring device with such a flow cell. In the following, the term "device for holding a light guide" refers to the device shown by FIG. 3a, whereas the term "light guide holder" refers to a part of this device, namely that denoted by 10.

Figure 1:
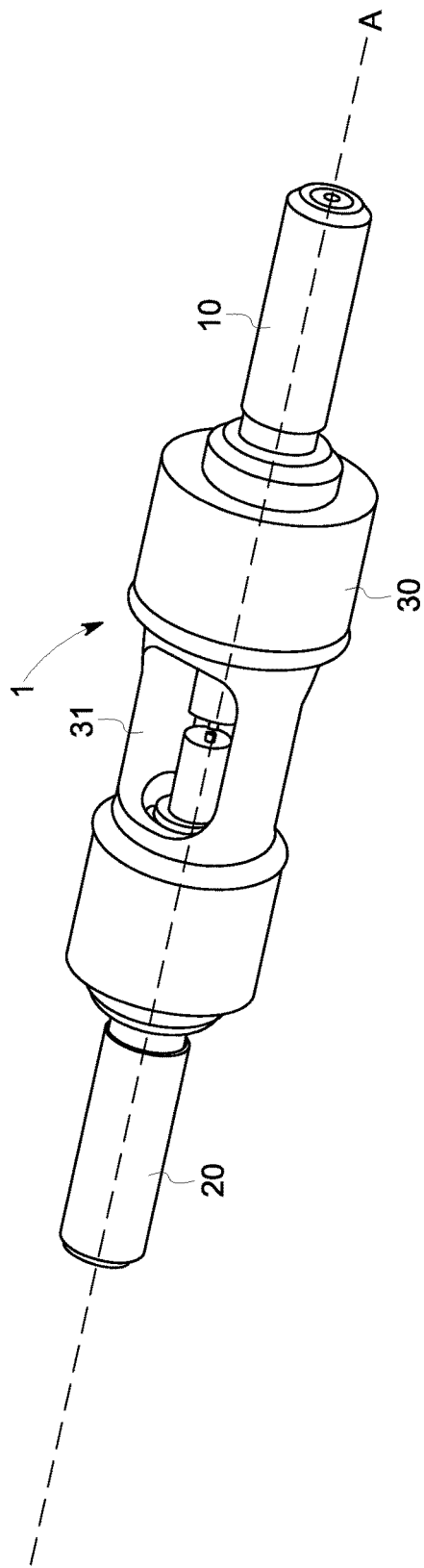
FIG. 1 shows a perspective view of an optical flow cell comprising a device for holding a light guide according to a preferred embodiment of the invention.

Thus, FIG. 1 discloses an optical flow cell 1 with a holder 30 that extends along an axis A and has a transversal through hole 31 arranged to allow a through flow of a sample fluid.

The optical flow cell 1 further comprises a first light guide holder 10 and a second light guide holder 20 that are arranged along said axis A. The optical flow cell 30 can be inserted into a measuring device, as will be described in more detail further below, and is able to detect the concentration of a substance in a flow of a fluid through the through hole 31.

Figure 2:
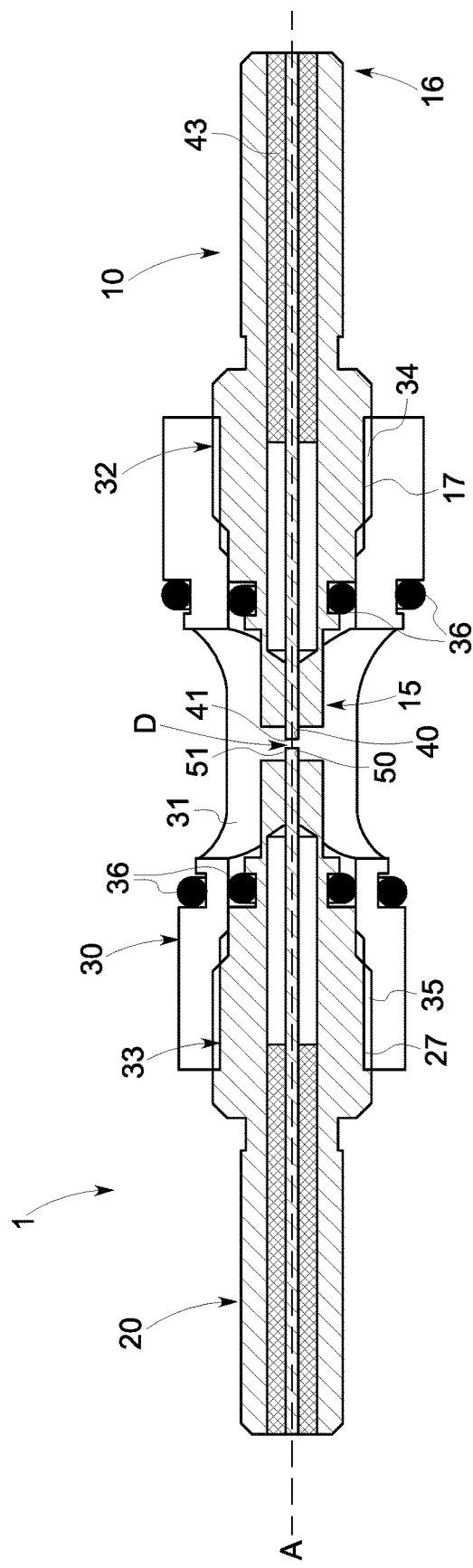
FIG. 2 shows a cross-sectional view of the optical flow cell of FIG. 1.

FIG. 2 shows the optical flow cell 1 of FIG. 1 in a cross-sectional view, showing that the first light guide holder 10 is mounted in a first hole 32 and the second light guide holder 20 is mounted in a second hole 33 along the axis A of the holder 30 and protrude into the through hole 31. Inside the first light guide holder 10 is an input light guide 40, for instance in the form of an optical fiber, with a light exit surface 41 through which light can be emitted. Similarly, the second light guide holder 20 comprises an output light guide 50 with a light entrance surface 51 through which light can be received and transmitted along the output light guide 50. The input light guide 40 and output light guide 50 are arranged in optical alignment, so that light emitted from the light exit surface 41 can be received by the light entrance surface 51. The light exit surface 41 and the light entrance surface 51 are further arranged at a first distance D from each other, and the first distance D is preferably 2 mm or less. It is, however, especially advantageous if the first distance D is very small, namely 0.2 mm or less, preferably 0.1 mm. This is advantageous in that a higher concentration of a substance flowing through the through hole 31 of the holder 30 can be detected with accuracy if the first distance D is kept small. The first distance D of the optical flow cell 1 is also commonly known as a pathway of the optical flow cell, and these terms will be used interchangeably below.

The holder 30 comprises a material with low thermal expansivity, i.e. with a thermal expansivity of 20×10-6 m/mK or less. Preferably, the holder 30 comprises titanium, but it can alternatively comprise another material such as ceramics.

The first light guide holder 10 and second light guide holder 20 are mounted in the first hole 32 and second hole 33, respectively, by screwing so that a holder thread 34, 35 of each hole 32, 33 interact with light guide holder threads 17, 27, respectively, and the light guide holders 10, 20 are fixed in the holder 30 as will be described in more detail further below. Sealing rings 36 are also provided to prevent leakage from the through hole 31.

FIG. 3a shows the first light guide holder 10, but it is to be noted that the second light guide holder 20 is similar to the first light guide holder 10 and that everything said with regard to the one also applies equally to the other.

Thus, the first light guide holder 10 is elongated and has a first end 15 and a second end 16, and a longitudinal through hole 11 with a narrow portion 12 at the first end 15 and a wide portion 13 at the second end 16. The wide portion 13 ends in a tapering portion 14 that is connected to the narrow portion 12 so that a diameter of the longitudinal through hole 11 is smoothly decreased from a second diameter $d_2$ at the wide portion 13 to a first diameter $d_1$ at the narrow portion 12. Along an outer surface of the first light guide holder 10 is a threaded section 17 that is adapted to interact with a corresponding thread of the holder 30.

Inside the first light guide holder 10, the input light guide 40 is arranged along the entire length of the longitudinal through hole 11 so that the light exit surface 41 protrudes from the first end 15. This is advantageous since the smaller diameter of the input and output light guides 40, 50 compared to the diameter of the input and output light guides 40, 50 together with the first end of the first and second light guide holders 10, 20, respectively, allows for an improved flow between the light guides 40, 50.

The first diameter $d_1$ is only slightly larger than a diameter of the input light guide 40, preferably less than 10% larger, so that the input light guide is securely held and movements of the input light guide 40 are prevented. Typically, the diameter of the input light guide 40 is about 400 nm. The input light guide 40 is held by a tube 43, preferably a tube that surrounds the input light guide 40. The purpose of the tube 43 is to guide the input light guide 40 during mounting in the first light guide holder 10 and it is advantageous if the tube 43 is stiff and resilient so that said mounting is facilitated, as will be described in more detail below.

In order to fix the input light guide 40 inside the first light guide holder 10, at least a part of the longitudinal through hole 11 is filled with a substance that surrounds the input light guide 40 and prevents movements in relation to the first light guide holder 10. The substance can be an adhesive, for instance an inert adhesive with a low viscosity, preferably a viscosity of 400 cPs or less. One example of a suitable adhesive is an epoxy adhesive such as Epotek® adhesive sold by Epoxy Technology, Inc.

FIG. 3b shows the first light guide holder 10 in a planar view, with the output light guide 40 extending from the first end 15 and the threaded section 17 clearly shown. A flange 18 may also be provided along an outside of the first light guide holder 10, to separate the threaded section 17 from a handle 19 by which the first light guide holder 10 can be held during mounting.

Figure 4A:
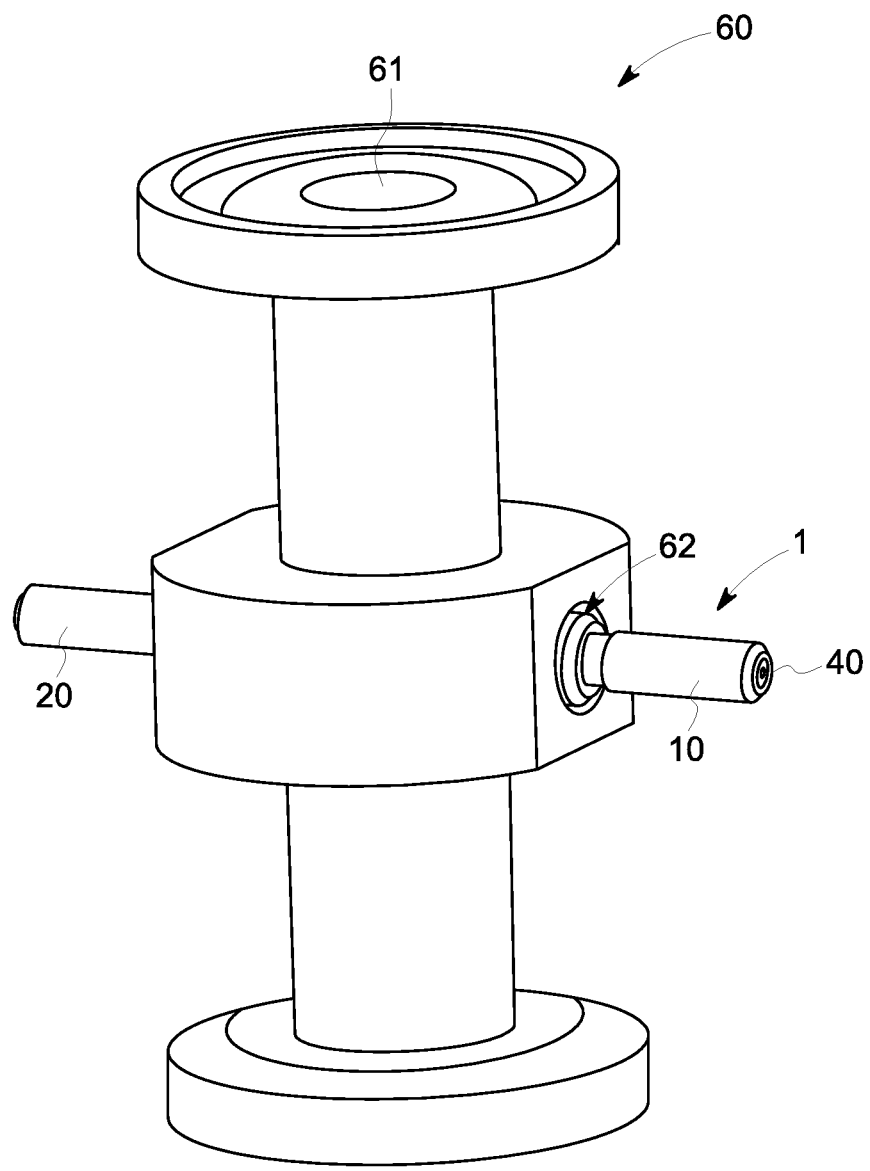
FIG. 4a shows a measuring device with the optical flow cell of FIG. 1-2.
Figure 4B:
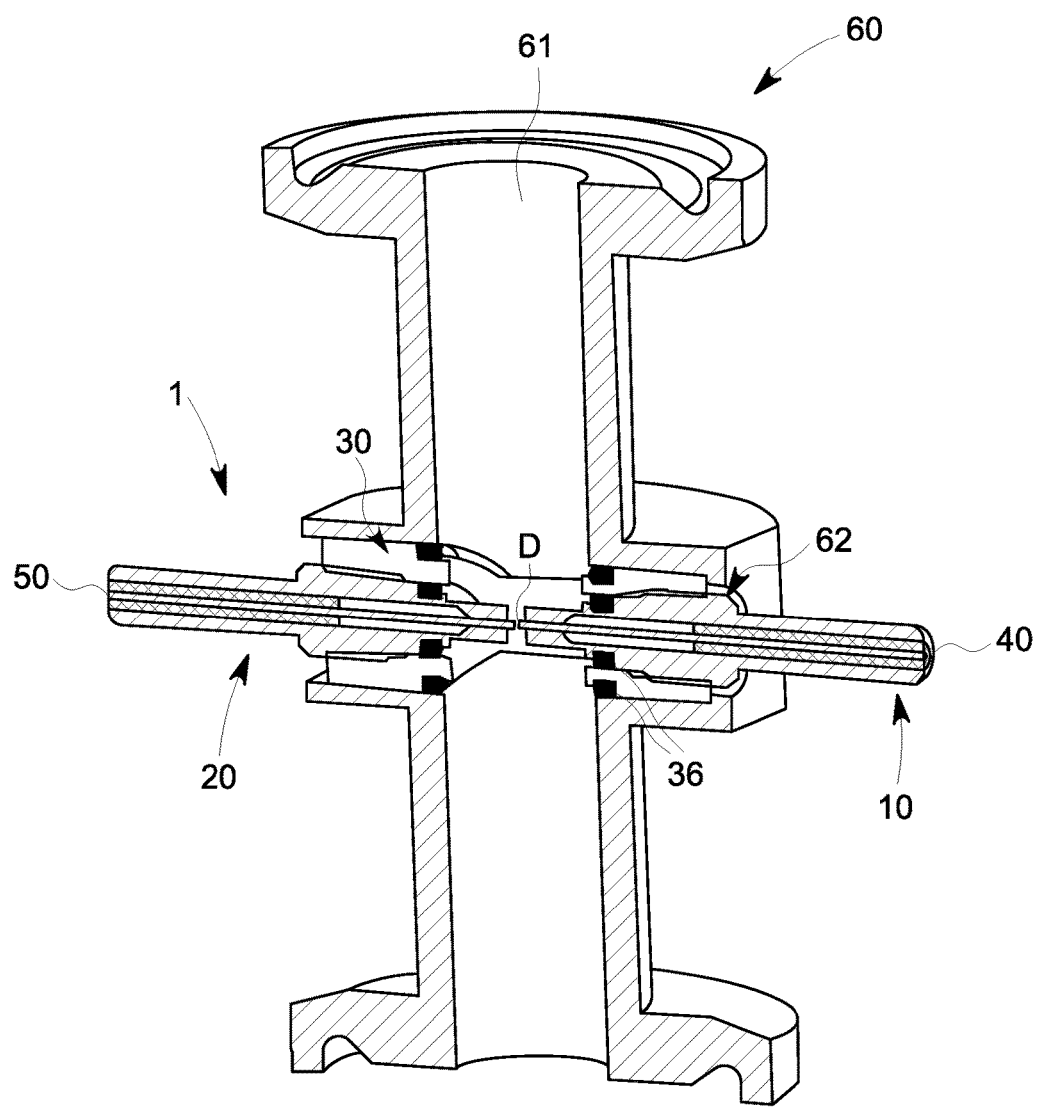
Figure 5:
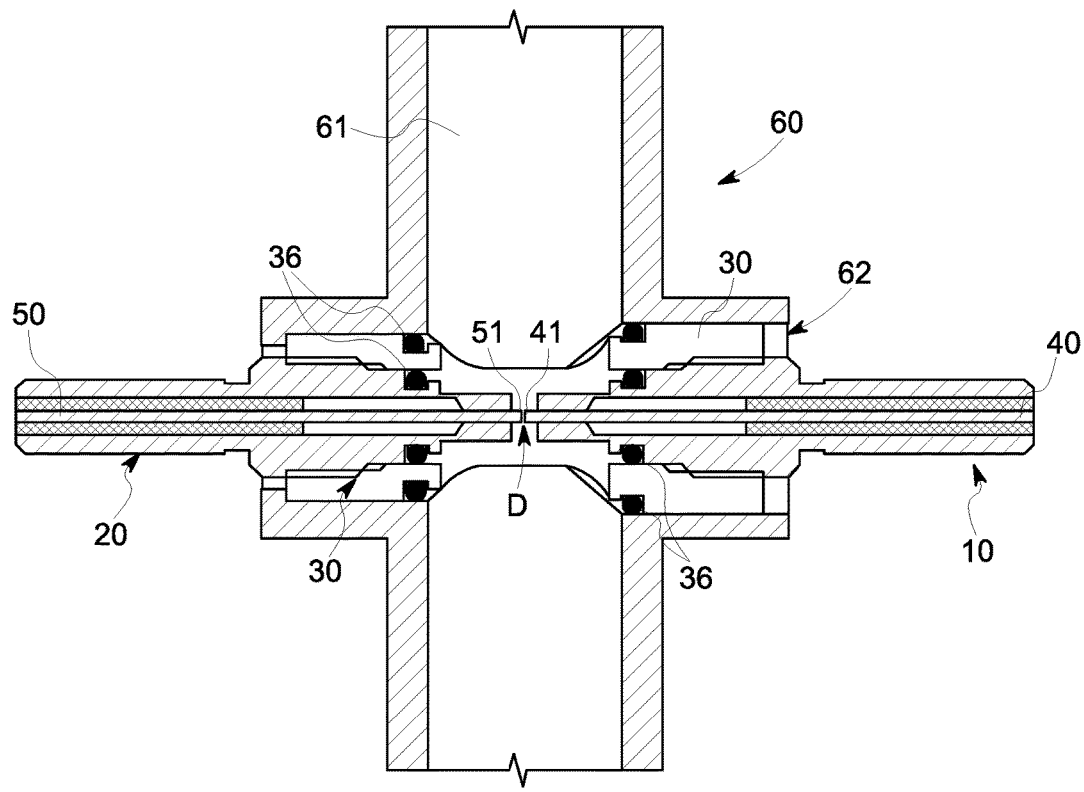
FIG. 5 shows a cross-sectional view of the measuring device of FIG. 4a-4b with the optical flow cell of FIG. 1-2 having a device for holding a light guide.
Figure 6:
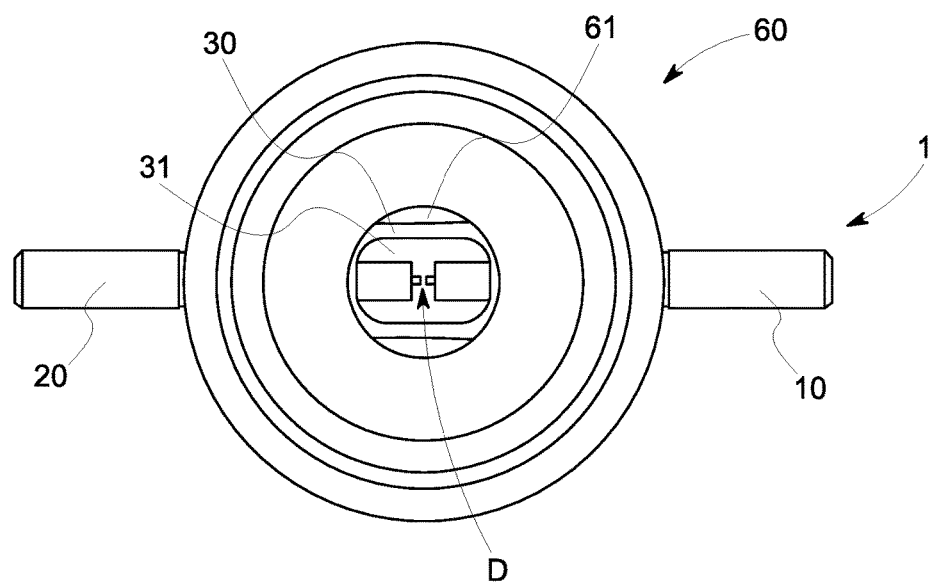

FIGS. 4a and 4b disclose a measuring device 60 in which an optical flow cell 1 is mounted for performing measurements on a substance flowing through a flow channel 61 that extends through the measuring device 60. The measuring device 60 has an optical flow cell mounting site 62 that is able to receive an optical flow cell 1 according to the invention so that the transversal through hole 31 of the holder 30 coincides with the flow channel 61 and a fluid can flow through the holder 30 and pass the output and input light guides 40, 50 to allow a detection of a substance in the fluid. In FIG. 5, the optical flow cell 1 is shown mounted in the measuring device 60, with the transversal through hole 31 aligned with the channel 61 to allow a flow through the optical flow cell 1 and thereby measurements on the portion of the flow that passes through the first distance D between the output light guide 40 and the input light guide 50. The sealing rings 36 are also shown and serve to prevent leakage along the mounting site 62 and the first and second holes 32, 33. When mounted in a measuring device 60, the optical flow cell 1 is connected to a system (not shown) with suitable equipment for transmitting light to the output light guide 40, receiving light captured by the input light guide 50, analyzing said received light and presenting and/or storing data from the optical flow cell 1 as is well known in the art. FIG. 6 shows the measuring device 60 from one end of the channel 61, showing how the optical flow cell 1 is mounted to align the through hole 31 of the holder 30 with the channel 61 itself.

Figure 7:
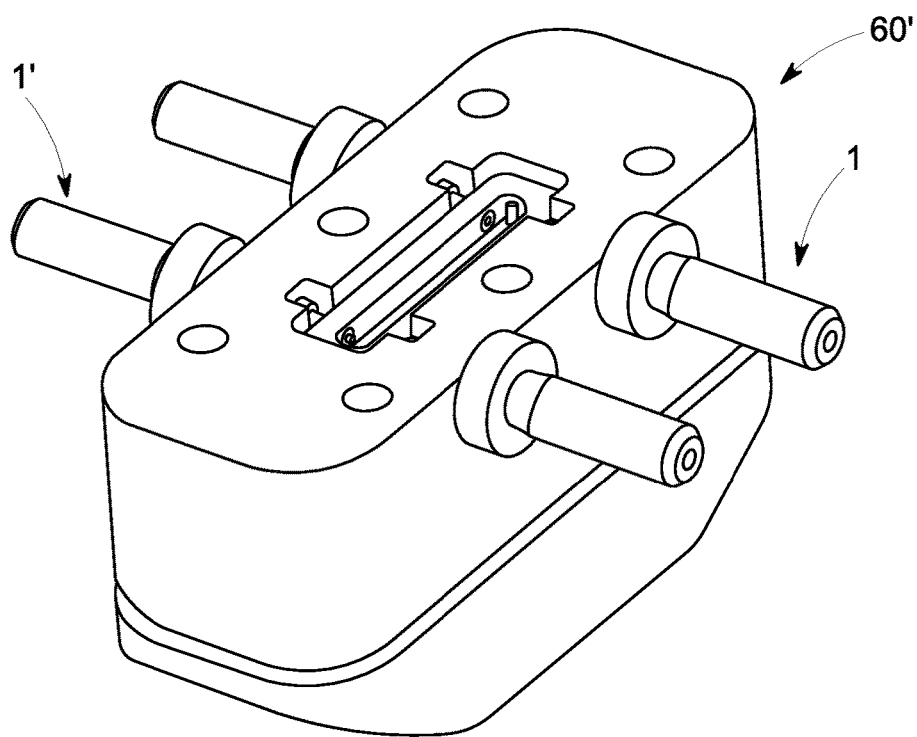
FIG. 7 shows a measuring device with two optical flow cells having light guide holders according to the invention.

In FIG. 7, a different measuring device 60' is shown with two optical flow cells 1, 1' according to the invention. The optical flow cells 1, 1' are similar in design and configuration, so that each component of a first optical flow cell 1 corresponds to a component of a second optical flow cell 1'. The optical flow cells 1, 1' may differ in the pathway D, however, so that a dual pathway measuring device 60' is created.

The mounting of the light guides 40, 50 in the light guide holders 10, 20 will now be described in more detail with reference to the Figures, and it is to be noted again that what is said with reference to the first light guide holder 10 and the output light guide 40 can also be applied to the second light guide holder 20 and the input light guide 50.

Thus, the output light guide 40 is provided and mounted in the first light guide holder 10 by insertion through the second end 16 and is guided into the narrow portion 12 by the tapering portion 14. The output light guide 40 is allowed to protrude from the first end 15. Then, the longitudinal through hole 11 is filled with the substance, preferably an inert adhesive as mentioned previously. After the substance has been applied, the tube 43 is mounted around the output light guide 40 from the second end 16, forcing the substance to penetrate the narrow portion 12 as well as between the output light guide 40 and the tube 43 and between the tube 43 and the first light guide holder 10. The substance is hardened and surplus substance is removed, and then the light exit surface 41 and an opposing end of the output light guide 40 at the second end 16 are polished to interfere as little as possible with the forthcoming measurements. Thanks to the inert nature of the substance, it can be present within the measuring device 60 without reacting with the flow. It is also advantageous for the substance to have a low viscosity, preferably less than 400 cPs, to allow for easy insertion of the tube 43.

The mounting of the optical flow cell 1 will now be described in more detail. After the input light guide 40 has been mounted in the first light guide holder 10 and the output light guide 50 has been mounted in the second light guide holder 20, as described above, the holder 30 is provided. The first light guide holder 10 is inserted through the first hole 32 by screwing so that the first light guide holder thread 17 interacts with the holder thread 34. Similarly, the second light guide holder 20 is inserted through the second hole 33 by screwing, wherein the second light guide holder thread 27 interacts with the holder thread 35. During the insertions, the through hole 31 of the holder is closely observed, and the screwing of each light guide holder 10, 20 is performed until the first distance D between the light exit surface 41 and the light entrance surface 51 is at a desired value, such as 0.1 mm. Thanks to the close observation, for instance through a microscope or similar equipment, the first distance D can be determined within small tolerances, and when the desired value has been achieved, the first light guide holder 10 and second light guide holder 20 are fixed in relation to the holder 30, for instance by applying an adhesive to the threads 17, 34, 27, 35 so that further movements are prevented. The sealing rings 36 can be applied to the first and second light guide holders 10, 20 and the holder 30 before mounting. The holder 30 further has a larger external diameter where the first light guide holder 10 is held than where the second light guide holder 20 is held. This is to facilitate mounting at the optical flow cell mounting site 62.

The mounting of the optical flow cell 1 in the measuring device 60 is thus performed by inserting the optical flow cell 1 into an optical flow cell mounting site 62 when the measuring device 60 is not in use, and to adjust the optical flow cell 1 until the transversal through hole 31 is aligned with the flow channel 61 so that the pathway D of the optical flow cell 1 can be exposed to a flow of a fluid through the flow channel 61. The output light guide 40 and input light guide 50 are then connected to the system as mentioned above and as is well known in the art, and the measuring device 60 can be used as is also commonly known in the art.

When the optical flow cell 1 becomes damaged, dirty or simply clogged by the fluid in the flow channel 61, operation can be interrupted and the flow channel 61 drained, so that the optical flow cell 1 can be disconnected from the system and be removed from the measuring device 60. The optical flow cell 1 can then be cleaned and reinserted. If the optical flow cell 1 has been damaged, it can alternatively be discarded and a new optical flow cell inserted in the optical flow cell mounting site 62, so that operation can be resumed with the same precision and accuracy as before damages or clogging occurred. Of course, if a different pathway D is desired, the optical flow cell 1 can simply be removed as described herein and replaced by a similar optical flow cell with a different pathway D. Thereby, measurements of substances of varying concentration in the fluid can be performed by the same measuring device 60 in an easy and convenient way and without requiring calibration.

The invention is not to be seen as limited by the exemplary applications described above, but can be used in different types of devices as is readily apparent to the person skilled in the art.

The invention claimed is:

1. A method for manufacturing a device for holding a light guide, the method comprising:
   providing a light guide holder having a first end and a second end connected by a longitudinal through hole comprising a first portion at the first end having a first diameter and a second portion at the second end having a second diameter, the first diameter being smaller than the second diameter, and the first portion and the second portion being connected by a tapering portion;
   inserting a light guide into the through hole such that the light guide extends from the first end to the second end of the light guide holder;
   inserting a substance into at least part of the second portion;
   after inserting the substance into at least part of the second portion, inserting a tube into the through hole; and
   fixing the light guide in relation to the light guide holder by the substance.

2. The method according to claim 1, wherein the first diameter is less than 10% larger than a diameter of the light guide.

3. The method according to claim 1, wherein the light guide is fixed along a center of the through hole before the substance is inserted.

4. The method according to claim 1, wherein the substance is an adhesive.

5. The method according to claim 4, wherein the adhesive has a viscosity of 400 cPs or less.

6. The method according to claim 1, wherein inserting the light guide into the through hole comprises inserting the light guide at the second end and using the tapering portion to guide the light guide towards the first portion at the first end.

7. The method according to claim 1, wherein the substance is an inert adhesive.

8. The method according to claim 1, wherein the tube is inserted into the through hole after the light guide is inserted into the through hole.

9. The method according to claim 1, wherein inserting the tube into the through hole comprises inserting the tube between the light guide and the light guide holder.

10. The method according to claim 1, wherein the light guide has a light entrance surface and a light exit surface, and wherein fixing the light guide in relation to the light guide holder by the substance comprises fixing the light guide such that the light entrance surface is flush with the second end of the light guide holder and the light exit surface protrudes from the first end of the light guide holder.

11. A device for holding a light guide, the device comprising:
- a light guide holder comprising a longitudinal through hole extending from a first end to a second end of the light guide holder, the through hole comprising a first portion having a first diameter at the first end and a second portion having a second diameter at the second end, the first portion being connected to the second portion by a tapering portion, and the first diameter being smaller than the second diameter;
- a light guide mounted in the through hole, the light guide having a light entrance surface flush with the second end of the light guide holder and a light exit surface protruding from the first end of the light guide holder;
- a substance disposed within the through hole such that the light guide is fixed in relation to the light guide holder; and
- a tube disposed within the through hole and between the light guide and the light guide holder along at least part of the second portion.

12. The device according to claim 11, wherein the first diameter is less than 10% larger than a diameter of the light guide.

13. The device according to claim 11, wherein a portion of the substance is disposed within the first portion to fix the light guide in relation to the light guide holder.

14. The device according to claim 11, wherein the substance is an adhesive.

15. The device according to claim 14, wherein the adhesive has a viscosity of 400 cPs or less.

16. The device according to claim 11, wherein the substance is an inert adhesive.

17. The device according to claim 11, wherein the tube is fixed in relation to the light guide holder by the substance.

18. The device according to claim 11, wherein the tube has a first end and a second end, wherein the first end of the tube is disposed within the second portion and spaced apart from the tapered portion, and wherein the second end of the tube is flush with the second end of the light guide holder.

19. The device according to claim 11, wherein a portion of the substance is disposed radially between the tube and the light guide holder.

20. An optical flow cell for detecting a concentration of a substance in a flow of a sample fluid, the flow cell comprising:
- a holder extending along an axis and comprising a hole extending transverse to the axis, the through configured to allow the sample fluid to flow therethrough;
- a first device attached to the holder, the first device comprising:
  - a first light guide holder comprising a first through hole extending from a first end to a second end of the first light guide holder, the first through hole comprising a first portion having a first diameter at the first end of the first light guide holder and a second portion having a second diameter at the second end of the first light guide holder, the first portion of the first through hole being connected to the second portion of the first through hole by a first tapering portion, and the first diameter being smaller than the second diameter;
  - a first light guide mounted in the first through hole and aligned with the axis, the first light guide having a first light entrance surface flush with the second end of the first light guide holder and a first light exit surface protruding from the first end of the first light guide holder and disposed within the hole of the holder;
  - a first substance disposed within the first through hole such that the first light guide is fixed in relation to the first light guide holder; and
  - a first tube disposed within the first through hole and between the first light guide and the first light guide holder along at least part of the second portion of the first through hole; and
- a second device attached to the holder, the second device comprising:
  - a second light guide holder comprising a second through hole extending from a first end to a second end of the second light guide holder, the second through hole comprising a first portion having a third diameter at the first end of the second light guide holder and a second portion having a fourth diameter at the second end of the second light guide holder, the first portion of the second through hole being connected to the second portion of the second through hole by a second tapering portion, and the third diameter being smaller than the fourth diameter;
  - a second light guide mounted in the second through hole and aligned with the axis, the second light guide having a second light exit surface flush with the second end of the second light guide holder and a second light entrance surface protruding from the first end of the second light guide holder and disposed within the hole of the holder;
  - a second substance disposed within the second through hole such that the second light guide is fixed in relation to the second light guide holder; and
  - a second tube disposed within the second through hole and between the second light guide and the second light guide holder along at least part of the second portion of the second through hole.

* * * * *